(12) United States Patent
Yamasaki (10) Patent No.: US 8,409,849 B2
(45) Date of Patent: Apr. 2, 2013

(54) SMEAR SLIDE PREPARING APPARATUS AND SMEAR SLIDE PREPARING METHOD

(75) Inventor: Mitsuo Yamasaki, Kobe (JP)

(73) Assignee: Sysmex Corporation, Hyogo (JP)

( * ) Notice: Subject to any disclaimer, the term of this patent is extended or adjusted under 35 U.S.C. 154(b) by 444 days.

(21) Appl. No.: 12/334,998

(22) Filed: Dec. 15, 2008

(65) Prior Publication Data
US 2009/0155841 A1    Jun. 18, 2009

(30) Foreign Application Priority Data

Dec. 17, 2007  (JP) ................................ 2007-324611

(51) Int. Cl.
*C12M 3/00* (2006.01)
(52) U.S. Cl. .................................................. 435/288.3
(58) Field of Classification Search .................. None
See application file for complete search history.

(56) References Cited

U.S. PATENT DOCUMENTS

| | | | | |
|---|---|---|---|---|
| 4,087,154 A | * | 5/1978 | Menzel | 359/396 |
| 5,439,649 A | * | 8/1995 | Tseung et al. | 422/510 |
| 5,650,327 A | | 7/1997 | Copeland | |
| 5,665,312 A | * | 9/1997 | Sperber et al. | 422/81 |
| 6,214,560 B1 | * | 4/2001 | Yguerabide et al. | 506/3 |
| 6,268,208 B1 | * | 7/2001 | Kondo | 435/286.3 |
| 6,288,322 B1 | * | 9/2001 | Kawasaki et al. | 136/205 |
| 6,309,362 B1 | * | 10/2001 | Guirguis | 600/573 |
| 6,722,836 B2 | * | 4/2004 | Jager | 414/222.01 |
| 7,468,161 B2 | * | 12/2008 | Reinhardt et al. | 422/63 |
| 7,678,337 B2 | * | 3/2010 | Sage et al. | 422/510 |
| 7,901,630 B2 | * | 3/2011 | Putnam et al. | 422/73 |
| 2003/0087443 A1 | * | 5/2003 | Pressman et al. | 436/46 |
| 2006/0029519 A1 | * | 2/2006 | Nakaya et al. | 422/63 |

OTHER PUBLICATIONS

European Search Report issued in EP 2 072 993 dated Sep. 29, 2010.

* cited by examiner

*Primary Examiner* — Ann Lam
(74) *Attorney, Agent, or Firm* — Sughrue Mion, PLLC (57) ABSTRACT

The present invention is to present a smear slide preparing apparatus capable of properly providing sample-related information on a predetermined area of a slide glass even when glass shards and dust and the like are attached to the predetermined area. A smear slide preparing apparatus comprises: a smear section for smearing a sample on a slide glass; an attached matter removing section for removing attached matter which is attached to a sample-related information area of the slide glass; and a sample-related information providing section for providing sample-related information which is related to the sample on the sample-related information area of the slide glass, the attached matter having been removed from the sample-related information area.

12 Claims, 12 Drawing Sheets

SMEAR SLIDE PREPARING APPARATUS AND SMEAR SLIDE PREPARING METHOD

FIELD OF THE INVENTION

The present invention relates to a smear slide preparing apparatus and smear slide preparing method, and more specifically relates to a smear slide preparing apparatus and smear slide preparing method for preparing a smear slide by smearing a sample on a slide glass.

BACKGROUND

U.S. Patent Publication No. 2006/0029519, for example, discloses a conventional blood smear slide preparing apparatus for preparing a blood smear slide by smearing blood on a slide glass.

U.S. Patent Publication No. 2006/0029519 discloses a blood smear slide preparing apparatus for transporting a slide glass that is stored in a slide storing section, and smearing blood on the transported slide glass. In the blood smear slide preparing apparatus, a slide glass on which a blood is smeared is transported to a printing part configured by a thermal transfer printer, and sample-related information such as the sample number, patient name and the like is printed at a predetermined position on the slide glass (frosted area) by the printing part.

However, in the blood smear slide preparing apparatus disclosed in U.S. Patent Publication No. 2006/0029519, when attached matter such as glass shards and dust have become attached to the frosted area of the slide glass while the slide glass is transported from the slide storing section through the blood smearing position to the printing part, the sample-related information may be printed on the frosted area which contains the attached matter. In this case, the situation in which printing cannot be performed properly due to the attached matter in the blood smear slide preparing apparatus of U.S. Patent Publication No. 2006/0029519 must be considered. A smear slide preparing apparatus which is better capable of properly printing sample-related information is therefore desirable.

SUMMARY

A first aspect of the present invention is a smear slide preparing apparatus comprising: a smear section for smearing a sample on a slide glass; an attached matter removing section for removing attached matter which is attached to a sample-related information area of the slide glass; and a sample-related information providing section for providing sample-related information which is related to the sample on the sample-related information area of the slide glass, the attached matter having been removed from the sample-related information area.

A second aspect of the present invention is a smear slide preparing method, comprising steps of: smearing a sample on a slide glass; transporting the slide glass through a first position to a second position; automatically removing attached matter which is attached on a sample-related information area of the slide glass at the first position; and automatically providing sample-related information on the sample-related information area of the slide glass at the second position.

DETAILED DESCRIPTION OF THE EMBODIMENT

The embodiments of the present invention are described hereinafter based on the drawings.

The general structure of a blood smear slide preparing apparatus 100 of the embodiment is first described below with reference to FIGS. 1 through 12.

Figure 1:
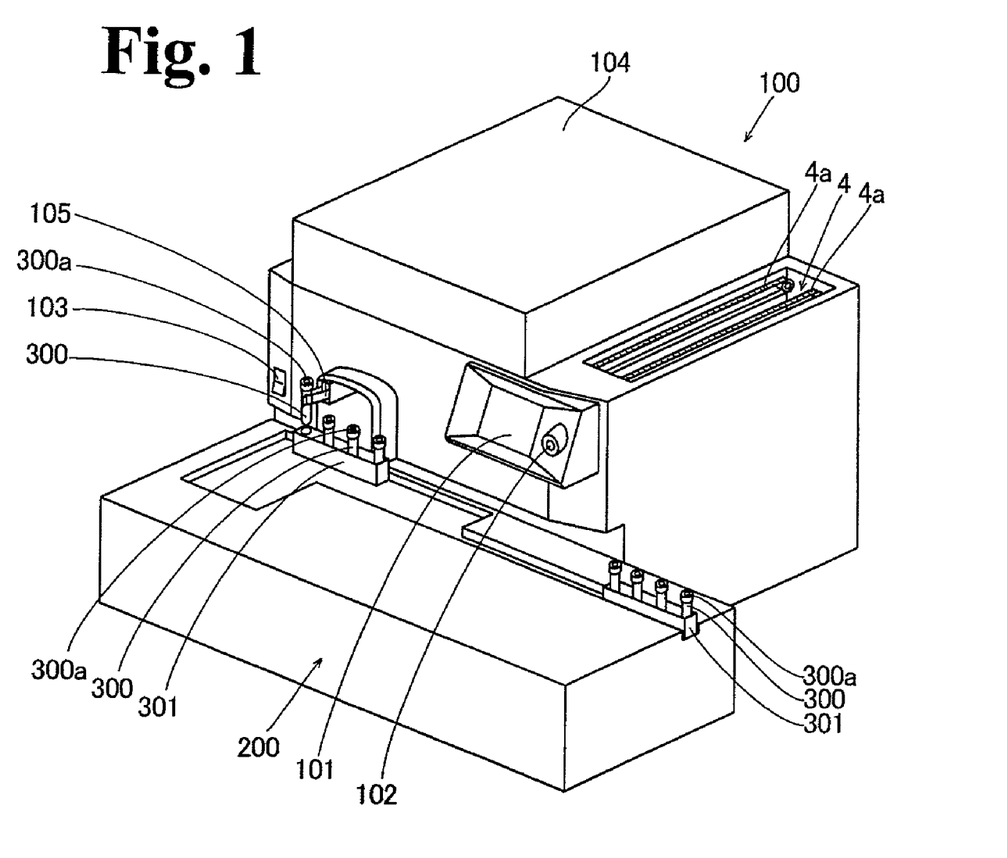
FIG. 1 is a perspective view showing the general structure of an embodiment of the blood smear slide preparing apparatus of the present invention.

The blood smear slide preparing apparatus 100 of the present embodiment is an apparatus for preparing blood smear slides by smearing, on a slide glass, the blood contained in a test tube 300 which is transported by a transporting device 200, as shown in FIG. 1. The blood smear slide preparing apparatus 100 is configured so that two types of smear slides are prepared, that is, an automatic analysis blood smear slide which can be analyzed by a blood cell automatic analyzer that is not shown in the drawing, and a visual blood smear slide which can be analyzed visually.

The transporting device 200 is disposed on the front surface side of the blood smear slide preparing apparatus 100, and is configured so that a sample rack 301 which holds test tubes 300 containing blood is transported automatically to the blood smear slide preparing apparatus 100. The blood smear slide preparing apparatus 100 includes a display and operation section 101 which is configured by a touch panel or the like, a start switch 102, power switch 103, and cover 104. The blood smear slide preparing apparatus 100 is also provided with a hand member 105 for transporting the test tubes 300 containing blood from the transporting device 200 side to the blood smear slide preparing apparatus 100 side. A rubber stopper 300a is fitted on the test tube 300 containing blood.

Figure 2:
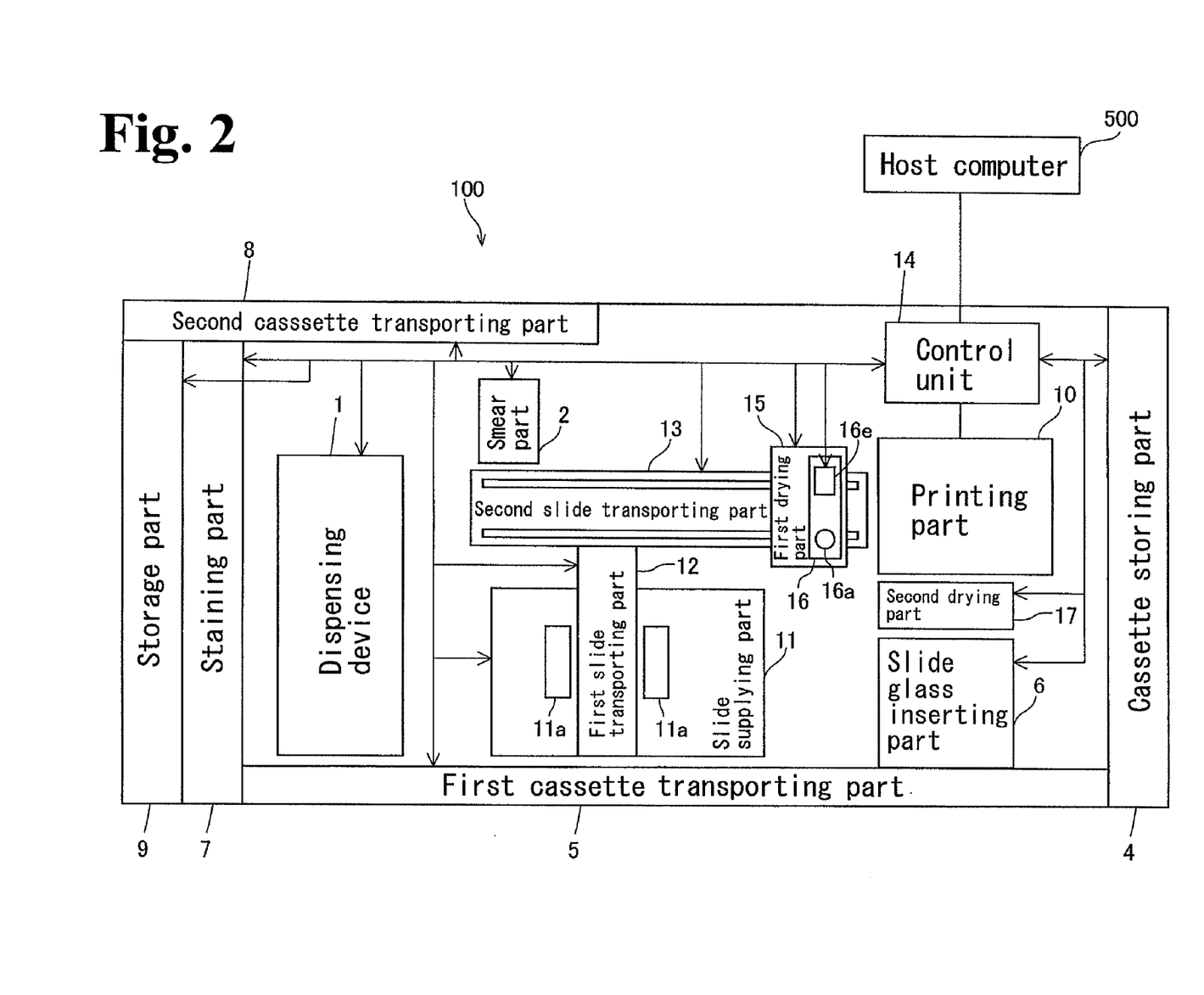
FIG. 2 is a block diagram of the blood smear slide preparing apparatus of the embodiment shown in FIG. 1.

The blood smear slide preparing apparatus 100 is configured by an dispensing device 1, smear section 2, resin cassette 3 (refer to FIG. 3), cassette storing part 4, first cassette transporting part 5, slide glass inserting part 6, staining part 7, second cassette transporting part 8, and storage part 9. The blood smear slide preparing apparatus 100 is also configured by a printing part 10, slide glass supplying part 11, first slide transporting part 12, second slide transporting part 13, control unit 14, first drying part 15, attached matter removing section 16, and second drying part 17. As shown in FIG. 2, a host computer 500 is connected to the control unit 14.

Figure 3:
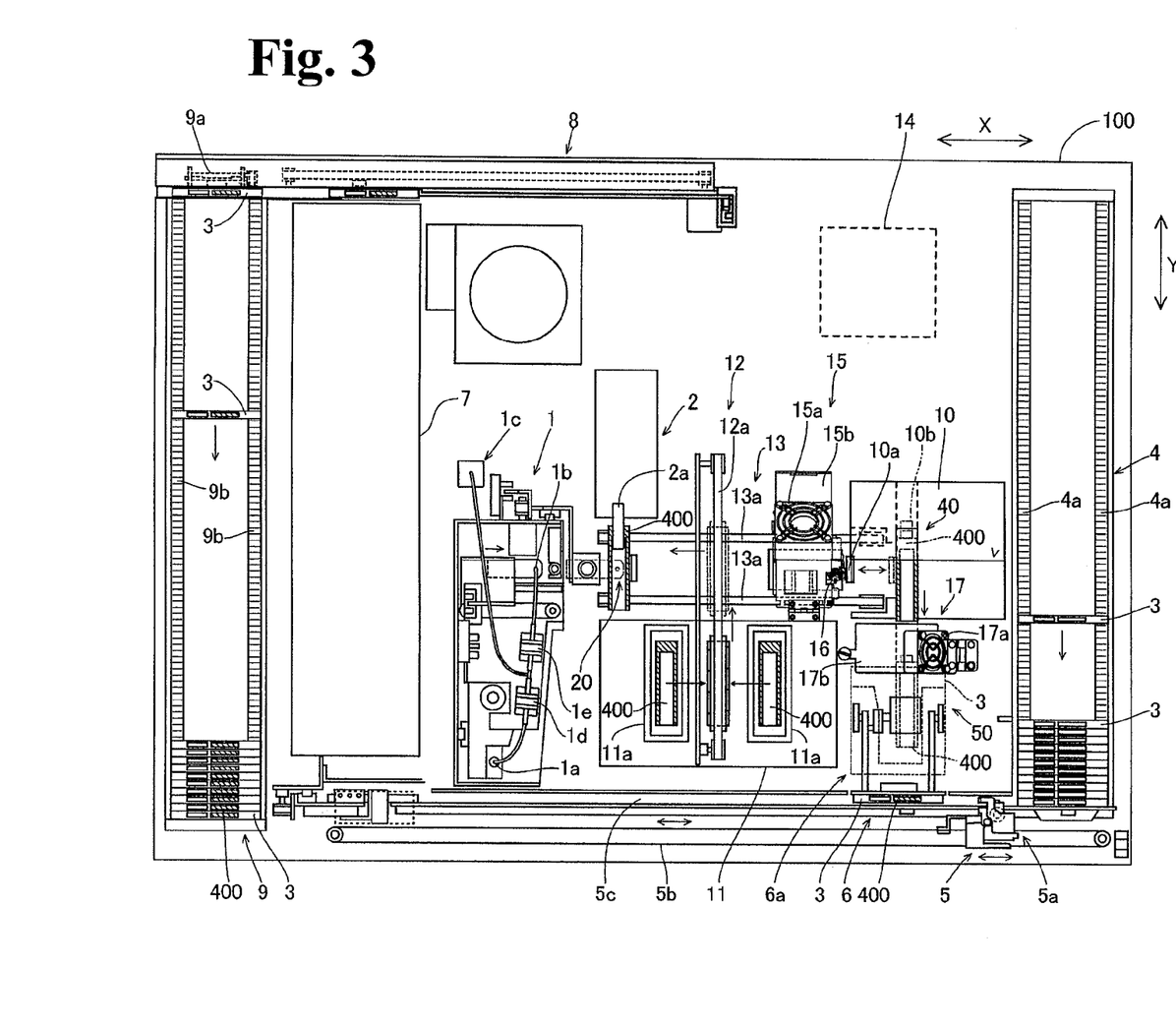
FIG. 3 is a top plan view showing the internal structure of the blood smear slide preparing apparatus of the embodiment shown in FIG. 1.

The dispensing device 1 has the functions of aspirating blood from the test tube 300 which has been transported to the blood smear slide preparing apparatus 100 side by the hand member 105 (refer to FIG. 1), and dripping the aspirated blood on a slide glass 400 at the dispensing and smearing position 20. As shown in FIG. 3, the dispensing device 1 includes a piercer (aspirating needle) 1a for aspirating the blood from the test tube 300, pipette 1b for dispensing the aspirated blood to the slide glass 400, syringe pump 1c which is connected to the piercer 1a and the pipette 1b, valve 1d for opening and closing the flow path between the piercer 1a and the syringe pump 1c, and valve 1e for opening and closing the flow path between the pipette 1b and the syringe pump 1c. The dispensing device 1 has the functions of dispensing the same blood (sample) to two respective slide glasses 400, and regulating the amount of the dispensed blood to an amount corresponding to the blood smear slide used for automatic analysis, and an amount corresponding to the blood smear slide used for visual analysis.

The smear section 2 is provided to smear the blood dripped on the slide glass 400. As shown in FIG. 3, the smear section 2 includes a drawing glass 2a, and is configured so as to smear the blood dispensed onto the slide glass 400 using the drawing glass 2a. Specifically, the drawing glass 2a is configured to be movable to a position at which the drawing glass 2a is in contact with the slide glass 400 at the dispensing and smearing position 20, and configured so as to smear the blood on the slide glass 400 by moving the drawing glass 2a in the length direction of the slide glass 400.

Figure 5:
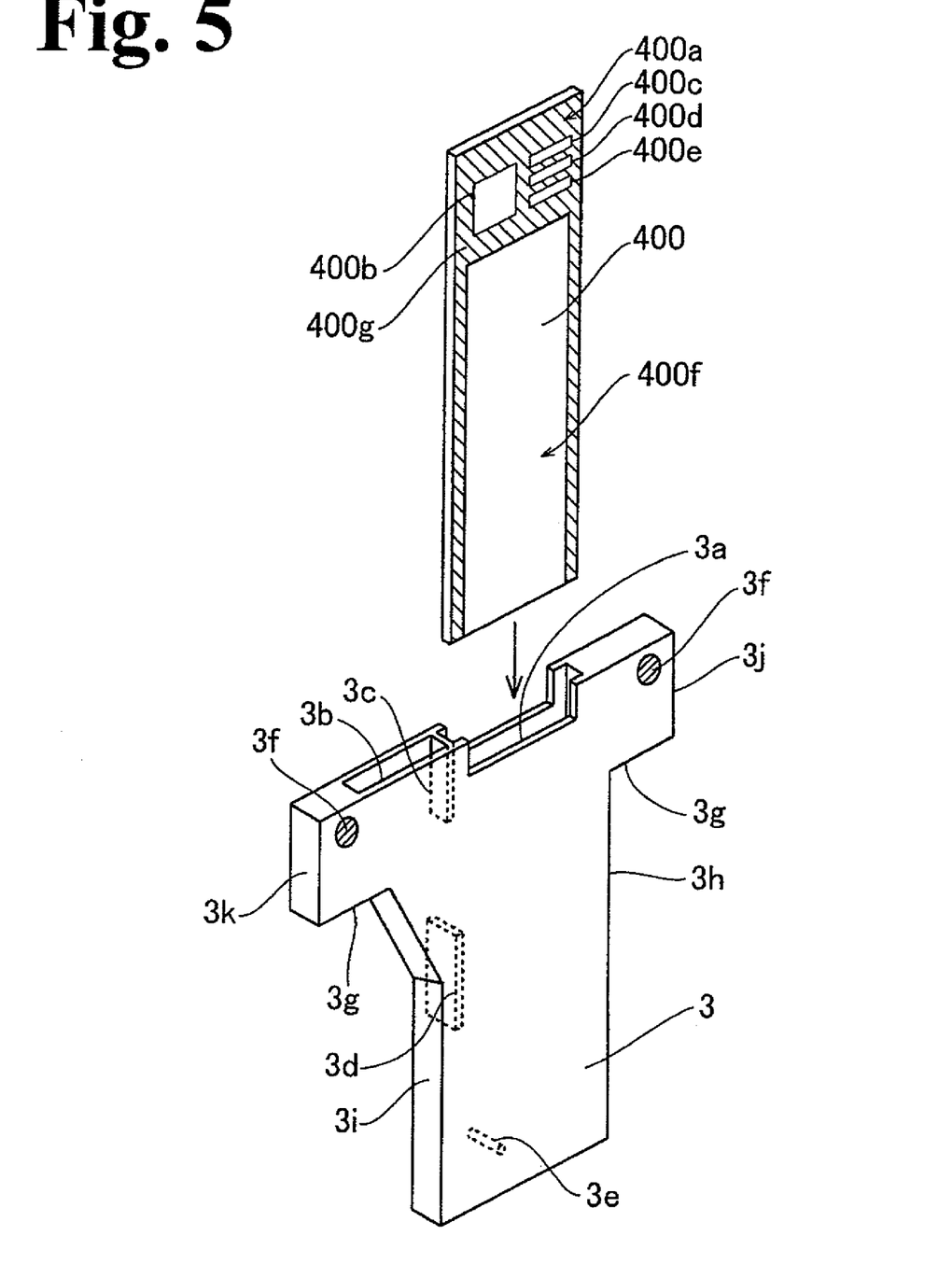
FIGS. 5 and 6 are perspective views of a cassette and a slide glass used in the blood smear slide preparing apparatus of the embodiment shown in FIG. 1.
Figure 6:
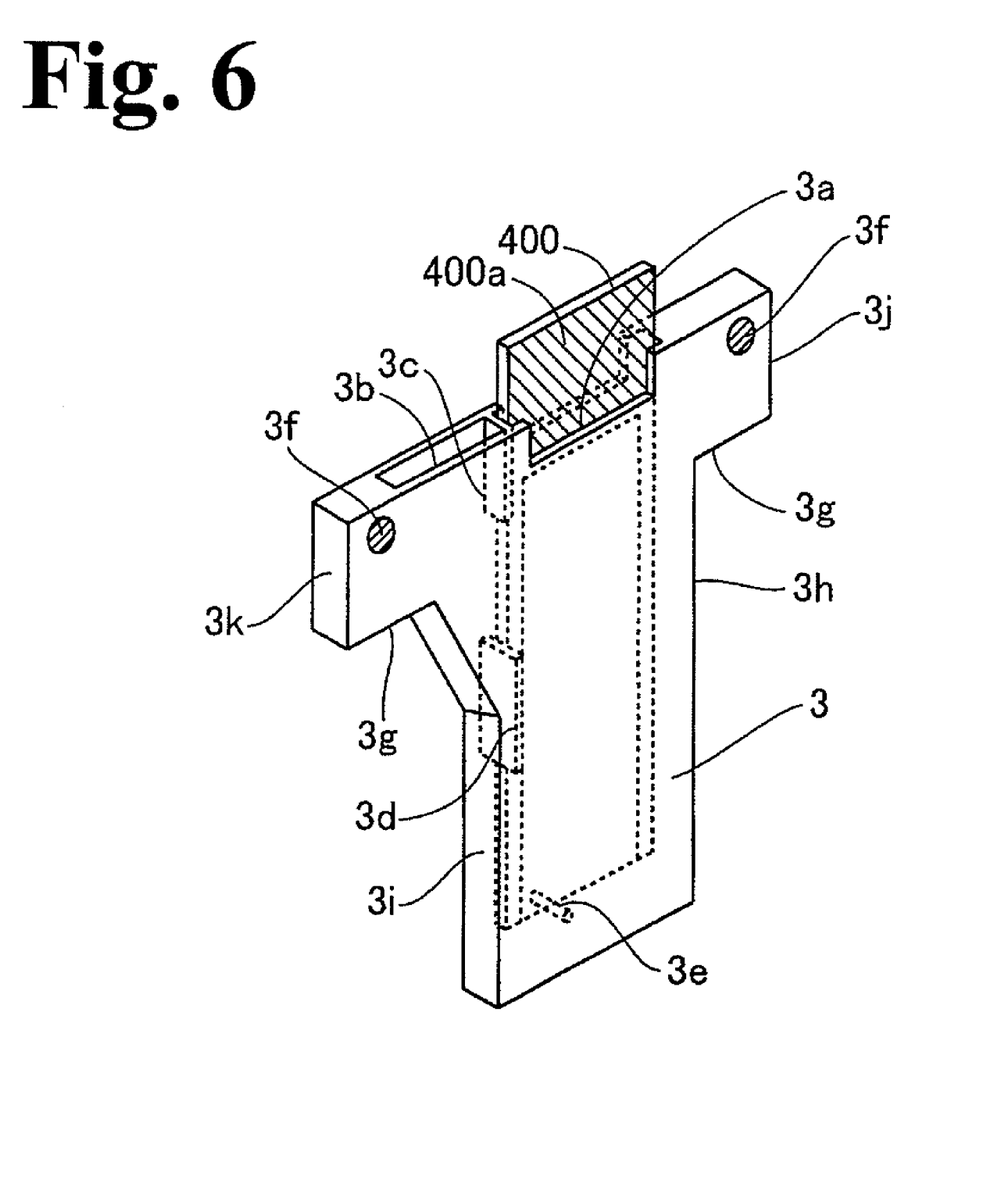

As shown in FIGS. 5 and 6, the resin cassette 3 is configured so as to be capable of accommodating the smeared slide glass 400 and a liquid (staining liquid) used in a staining process. Specifically, the cassette 3 includes a slide glass receiving orifice 3a, staining liquid receiving orifice 3b, partitions 3c and 3d, slide glass support 3e, two magnetic members 3f configured of a metal which can be attracted to a magnet, transport belt engaging part 3g, side surfaces 3h and 3i, and side surfaces 3j and 3k. The slide glass receiving orifice 3a and the staining liquid receiving orifice 3b are internally connected. The side surfaces 3j and 3k respectively protrude from the side surfaces 3h and 3i by a predetermined amount, and are disposed at the top part of the cassette 3.

As shown in FIG. 3, a cassette storing part 4 is provided for the insertion of the cassette 3, and includes a feed belt 4a.

The first cassette transporting part 5 is provided for transporting the cassette 3 which has been received from the cassette storing part 4 to the slide glass inserting part 6 and staining part 7. The first cassette transporting part 5 includes a cassette transporting member 5a which is movable in a horizontal direction, drive belt 5b for moving the cassette transporting member 5a in the horizontal direction, and transport path 5c for transporting the cassette 3 which has been supplied from the cassette storing part 4.

The slide glass inserting part 6 is provided for inserting the smeared and printed slide glass 400 into the slide glass receiving orifice 3a of the cassette 3. The slide glass inserting part 6 includes a cassette moving device 6a for disposing the cassette 3 in a horizontal direction to attain a state in which the slide glass 400 can be inserted.

The staining part 7 is provided for staining the smeared slide glass 400 by supplying a staining liquid to the staining liquid receiving orifice 3b of the cassette 3 which has been transported by the cassette transporting member 5a.

The second cassette transporting part 8 is configured so as to be capable of moving the cassette 3 which accommodates a stained slide glass 400 to both a blood cell automatic analyzer that is not shown in the drawing, and to the storage part 9 of the blood smear slide preparing apparatus 100. The second cassette transporting part 8 is also configured so that the transporting of the cassette 3 which accommodates the stained slide glass 400 to the storage part 9, or the transporting to the blood cell automatic analyzer is controlled by the control unit 14.

The storage part 9 is provided for storing the cassette 3 which accommodates the slide glass 400 that has been stained by the staining part 7. Note that the stained slide glass 400 which is received in the storage part 9 is to be visually analyzed. A feed part 9a and a transport belt 9b are provided in the storage part 9.

Figure 4:
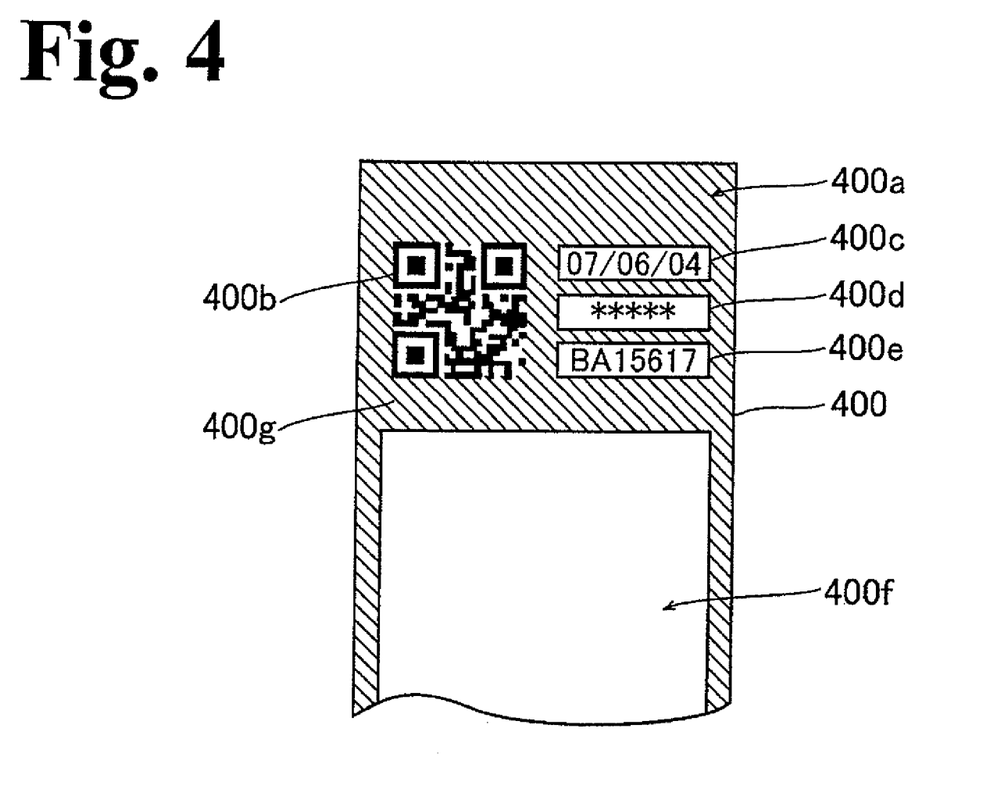
FIG. 4 is an enlargement of the frosted area of a slide glass used in the blood smear slide preparing apparatus of the embodiment shown in FIG. 1.

The printing part 10 is configured by a thermal transfer printer. The printing part 10 is provided for printing the sample-related information on the frosted area 400a (information surface region) of the slide glass 400 based on the sample information obtained from the host computer 500 (refer to FIG. 2), as shown in FIG. 4. Specifically, the printing part 10 prints, as sample-related information, a two-dimensional barcode 400b that contains the sample number, date, receiving number, and patient name and the like, and three lines of text data which include a date (07/06/04) 400c as attribute information that is included in the sample information, name (Sysmex) 400d, and sample number (BA15617) 400e. Note that the two-dimensional barcode may be a barcode which contains information bidirectionally in the horizontal direction and vertical direction when viewed planarly. A data matrix, QR code and the like may also be used as the two-dimensional barcode 400b which is printed on the frosted area 400a of the slide glass 400. The amount of information (cumulative number of letters) contained in the barcode 400b is a maximum of fifty half-width characters, and a maximum of 25 full-width characters.

The ink used by the printing part 10 for the two-dimensional barcode 400b and the text data (400c through 400e) printed on the frosted area 400a of the slide glass 400 is a durable ink which will not be dissolved by organic solvent such as alcohol and glycerin and the like which are used in the staining operation and microscopic examination.

The printing part 10 also has the functions of moving the slide glass 400 from the end of the feed belt 13a to the printing position 40, and moving the printed slide glass 400 to the slide inserting position 50 into the cassette 3. Specifically, as shown in FIG. 3, the printing part 10 includes horizontal direction moving piece 10a for moving the slide glass 400 in a horizontal direction (arrow X direction) from the end of the feed belt 13a to the printing position 40, and a vertical direction moving piece 10b for moving the slide glass 400 in a vertical direction (arrow Y direction) from the printing position 40 to the slide inserting position 50.

The slide glass supplying part 11 is provided for supplying the slide glass 400 prior to the dispensing of the blood to the first slide transporting part 12. The slide glass supplying part 11 also includes two slide storing parts 11a which store slide glasses 400.

The first slide transporting part 12 is provided for transporting the slide glass 400 which is supplied from the slide glass supplying part 11 to the second slide transporting part 13. The first slide transporting part 12 also includes a feed belt 12a, and a chuck which is not shown in the drawing for attachment to the feed belt 12a. The first slide transporting part 12 further has the function of supplying the slide glass 400 which is held by the chuck onto a feed belt 13a of the second slide transporting part 13.

The second slide transporting part 13 is provided for transporting the slide glass 400 which has been moved by the first slide transporting part 12 to the dispensing and smearing position 20, and transporting the blood smeared slide glass 400 to the drying positions 30a and 30b (refer to FIG. 8) of the first drying part 15, and the printing position 40 (refer to FIG. 3 of the printing part 10. As shown in FIG. 3, the second slide transporting part 13 is configured so that the slide glass 400 on the two feed belts 13a is transported in a direction (arrow X direction) perpendicular to the length direction of the slide glass 400. The second slide transporting part 13 also includes a lifting part 13b (refer to FIG. 9), and is configured so that the slide glass 400 transported to the drying positions 30a and 30b (refer to FIG. 8) can be lifted upward by the lifting part 13b to be separated from the feed belt 13a.

Figure 7:
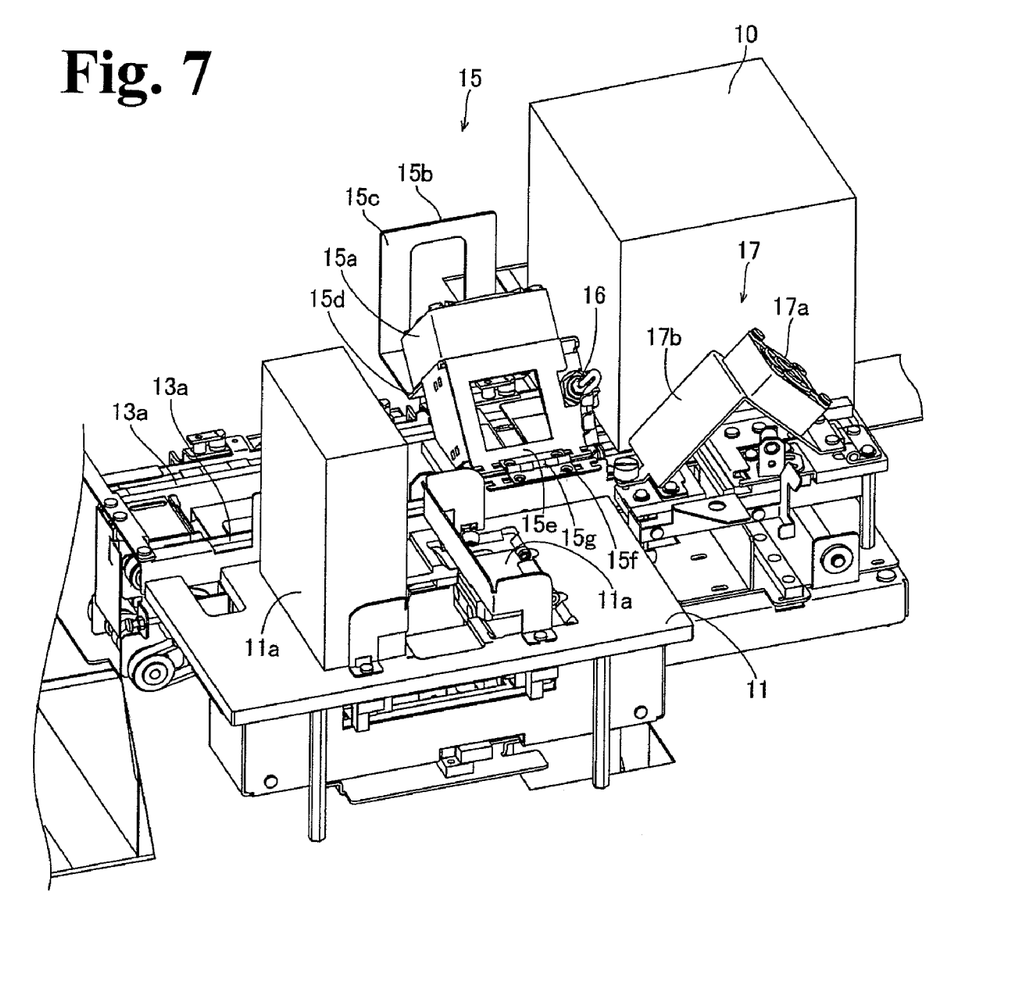
FIG. 7 is a perspective view showing the periphery of the attached matter removing section of the blood smear slide preparing apparatus of the embodiment shown in FIG. 1.
Figure 8:
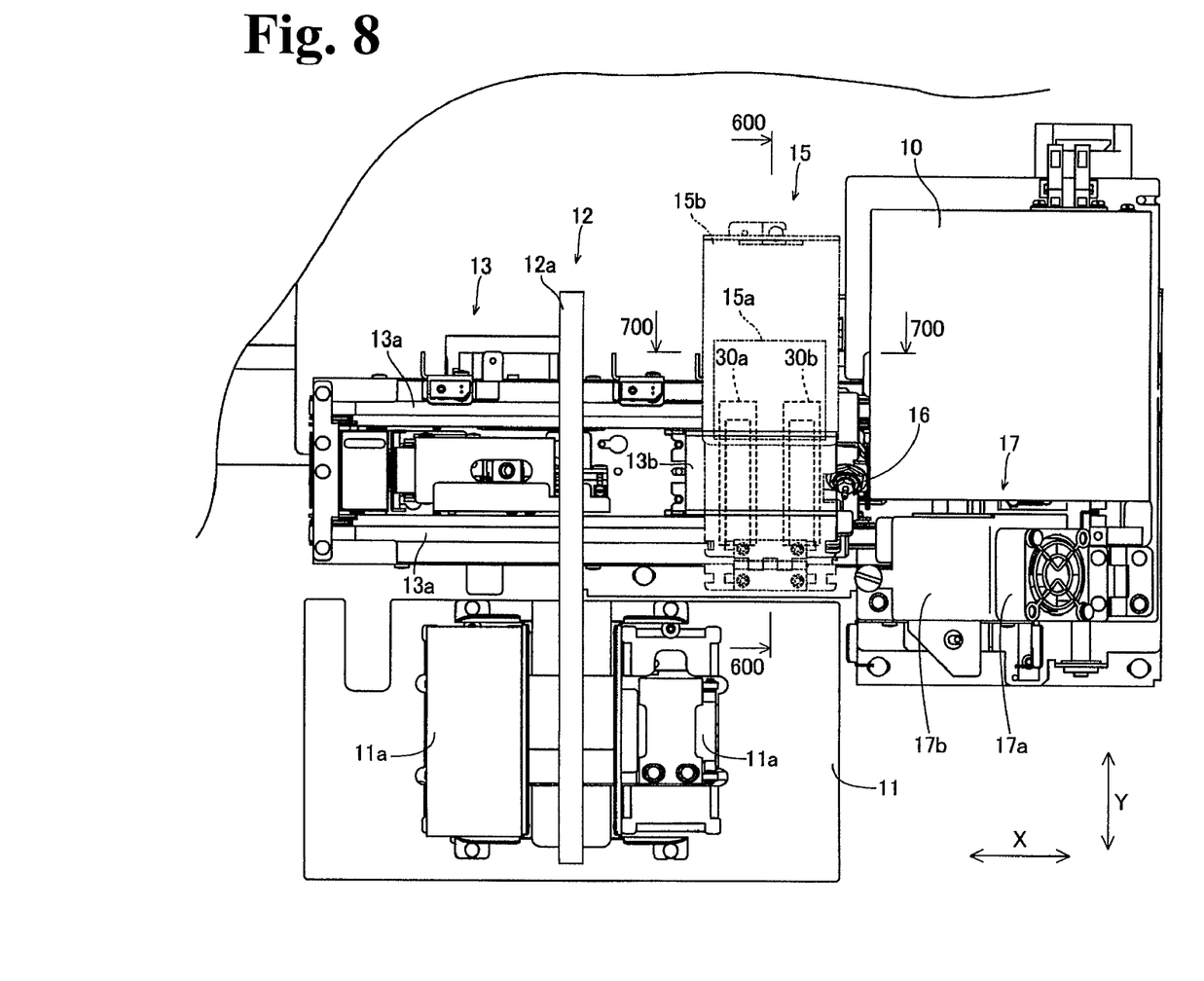
FIG. 8 is a top plan view showing the periphery of the attached matter removing section of the blood smear slide preparing apparatus of the embodiment shown in FIG. 1.
Figure 9:
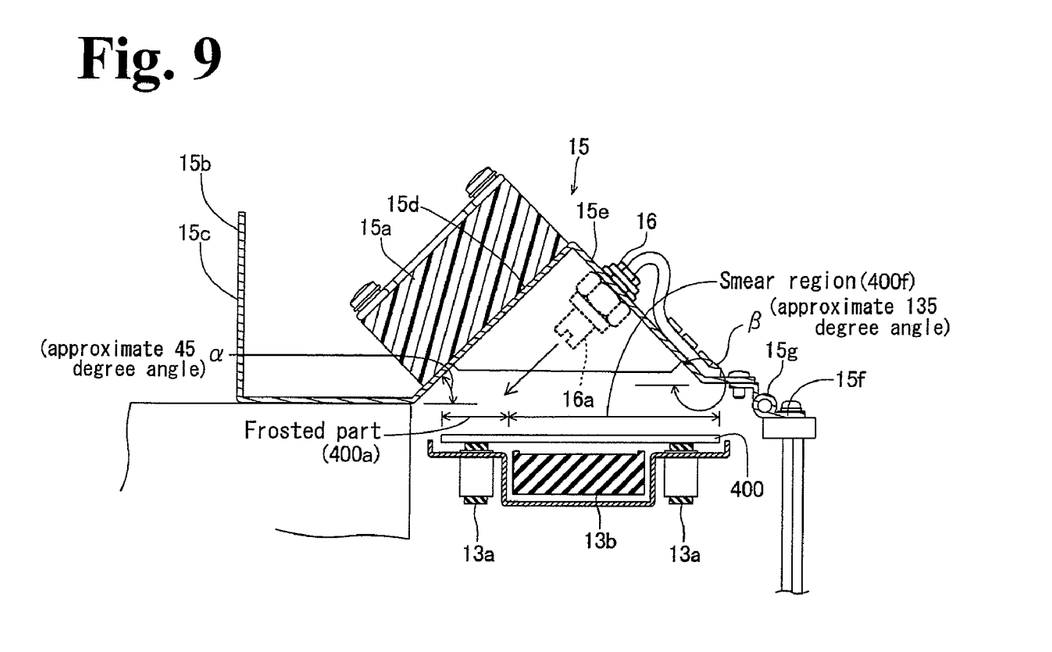
FIG. 9 is a cross sectional view along the 600-600 line of FIG. 8.
Figure 10:
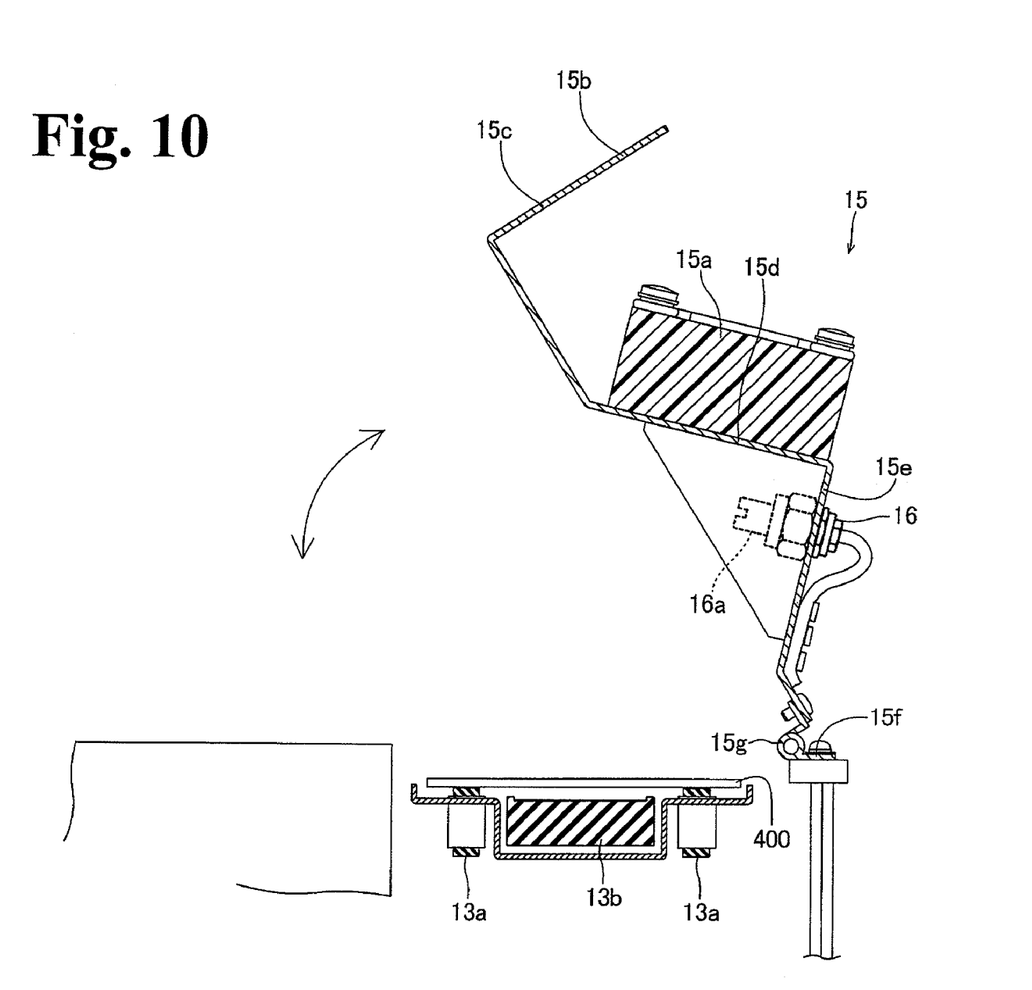
FIG. 10 is an illustration showing a fan mounting part and nozzle mounting part in a rotated state from the state shown in FIG. 9.

As shown in FIG. 3, the first drying part 15 includes a fan 15a, and a support part 15b which supports the fan 15a. The fan 15a is provided for drying the blood smeared on the slide glass 400 that has been transported to the drying positions 30a and 30b (refer to FIG. 8). As shown in FIG. 9, the support part 15b has a holder 15c, fan mounting part 15d, nozzle mounting part 15e, mounting part 15f, and moving part 15g. The support part 15b is disposed so as to straddle the two feed belts 13a of the second transporting part 13, as shown in FIGS. 7 through 9. The support part 15b is mounted at a predetermined position on the blood smear slide preparing apparatus 100 by the mounting part 15f, and is configured so as to be movable in vertical directions pivoting on the moving part 15g in the vicinity of the mounting part 15f, as shown in FIG. 10. The holder 15c is configured to be gripped by a user when the support part 15b is moved in the vertical directions, and the fan mount 16d and nozzle mounting part 15e are respectively configured to allow the mounting of the fan 15a and the nozzle 16a of the attached matter removing section 16.

In the present embodiment, when the support part 15b has been moved downward as shown in FIG. 9, the fan mounting part 15d is configured so as to be inclined at a predetermined angle α (approximately 45 degrees) relative to the surface of the slide glass 400 being transported by the second slide transporting part 13, and the nozzle mounting part 15e is configured so as to be inclined at a predetermined angle β (approximately 135 degrees) relative to the surface of the slide glass 400 being transported by the second slide transporting part 13. The fan 15a is thus supported by the support part 15b so as to be inclined at a predetermined angle α (approximately 45 degrees) relative to the surface of the slide glass 400 being transported to the drying positions 30a and 30b, and the nozzle 16a of the attached matter removing section 16 is supported so as to be inclined at an angle β (approximately 135 degrees (approximately 45 degrees in the opposite direction to the fan mounting part 15d)) relative to the surface of the transported slide glass 400.

In the present embodiment, the nozzle 16a of the attached matter removing section 16 is disposed between the printing position 40 (refer to FIG. 3) of the printing part 10, and the drying positions 30a and 30b (refer to FIG. 8) on the transport path of the slide glass 400. The nozzle 16a is also disposed so as to remove attached matter such as glass shards and dust attached to the frosted area 400a of the slide glass 400. The nozzle 16a is configured for removing attached matter by blowing on the frosted area 400a using a jet of removal air discharged at a predetermined pressure (approximately 0.25 MPa). As shown in FIG. 9, the nozzle 16a is configured so as to discharge a jet of removal air on the frosted area 400a of the slide glass 400 from a direction that is inclined at an angle β (approximately 135 degrees (approximately 45 degrees in opposite direction to the fan 15a)) relative to the surface of the transported slide glass 400. Since the attached matter removed from the frosted area 400a is blown to the opposite side from the smear region 400f side, adhesion of the blown matter on the smear region 400f of the slide glass 400 can therefore be prevented. Note that in the present specifications "attached" includes both the condition wherein glass shards and dust and the like are tightly adhered to the slide glass, and the condition wherein glass shards and dust and the like just rest on the slide glass.

Figure 11:
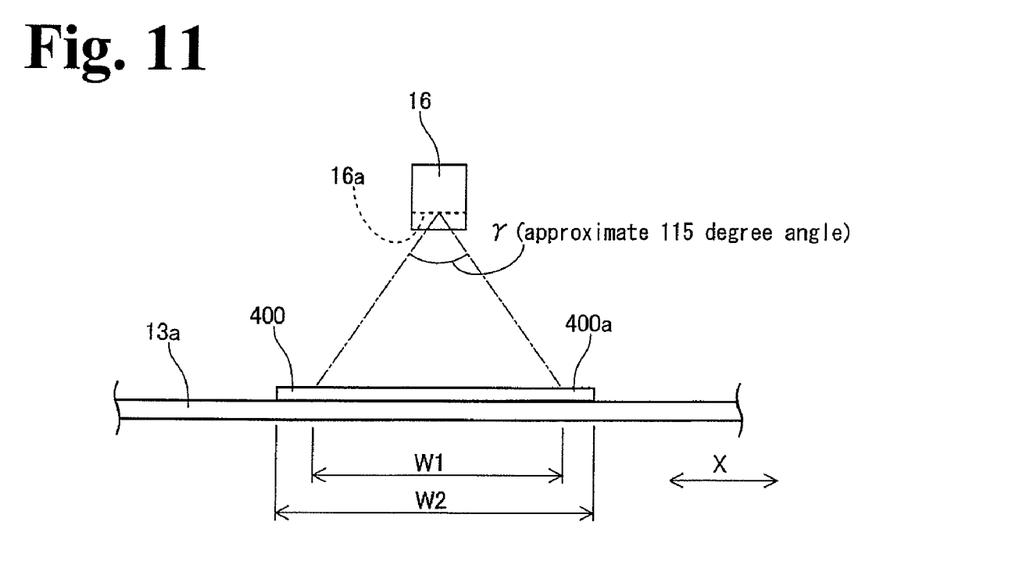
FIG. 11 is a cross sectional view along the 700-700 line of FIG. 8.

The nozzle 16a also is configured so as to discharge a jet of removal air in a range of a predetermined angle γ (approximately 115 degrees) in the transport direction (arrow X direction) of the slide glass 400, and the width W1 in the arrow X direction of the removal air reaching the frosted area 400a is smaller than the width W2 in the lateral direction of the slide glass 400, as shown in FIG. 11.

Figure 12:
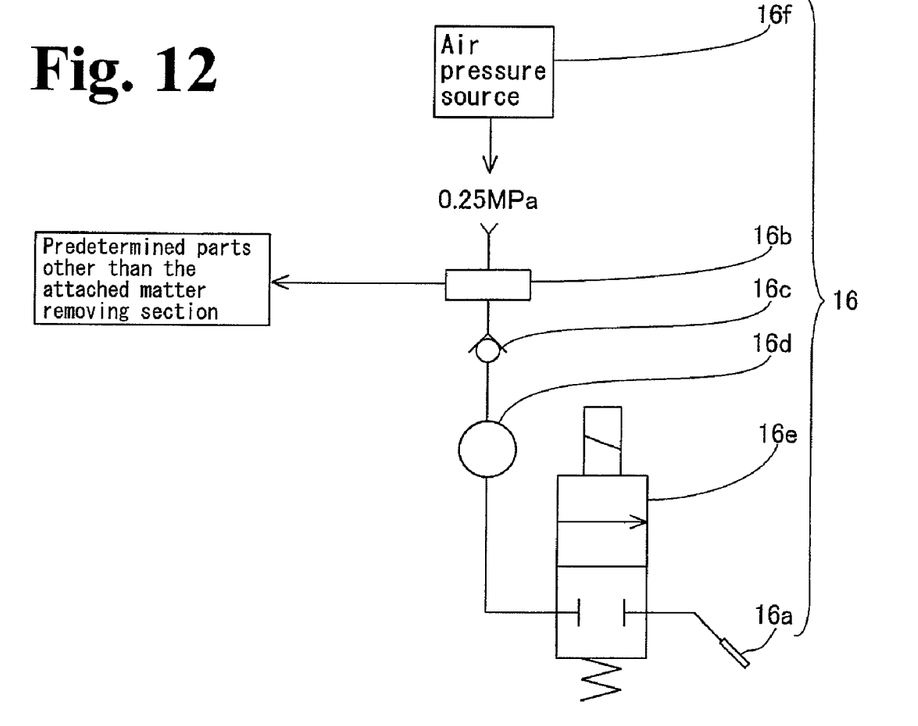
FIG. 12 is an illustration showing the attached matter removing section of the blood smear slide preparing apparatus of the embodiment shown in FIG. 1.

The constitution of the discharge of the removal air by the nozzle 16a of the attached matter removing section 16 is described in detail below. As shown in FIG. 12, the attached matter removing section 16 includes, in addition to the nozzle 16a, a flow path switching part 16b, check valve 16c, air tank 16d, valve 16e, and air pressure source 16f. The nozzle 16a is also connected to the air pressure source 16f through the flow path switching part 16b, check valve 16c, air tank 16d, and valve 16e. The air pressure source 16f is configured so as to supply an air pressure of approximately 0.25 MPa to predetermined parts outside the nozzle 16a and the attached matter removing section 16. The predetermined parts outside the attached matter removing section 16 include, for example, a washing part which is not shown in the drawing that is disposed in the staining part 7, and a chuck which is not shown in the drawing that is disposed in the first slide transporting part 12. The flow path switching part 16b is configured so as to switch the flow path of the air to supply the air pressure supplied from the air pressure source 16f to the predetermined parts outside the nozzle 16a or the attached matter removing section 16. The check valve 16c is configured so that the air arriving from the flow path switching part 16b side passes to the air tank 16d side, on the other hand, the check valve 16c is configured so that the air arriving from the air tank 16d side does not pass to the air path switching part 16b side. The air tank 16d is configured so that the air pressure supplied from the air pressure source 16f can be temporarily maintained. The valve 16e is configured so as to open and close the flow path of the air based on signals from the control unit 14. The nozzle 16a can thus discharge a jet of removal air via the air pressure within the air tank 16d when the valve 16e is opened. A sudden drop in the air pressure source 16f can be prevented even when the removal air is discharged from the nozzle 16a by using the air pressure within the air tank 16d for the removal air discharge.

The second drying part 17 is provided for drying the ink printed on the frosted area 400a of the slide glass 400. As shown in FIG. 7 the second drying part 17 includes a fan 17a, and a support part 17b which supports the fan 17a. The fan 17a is mounted on the support part 17b so as to be inclined at a predetermined angle δ (approximately 45 degrees) relative to the surface of the transported slide glass 400. The support part 17b is disposed so as to straddle the glass slide 400 being transported from the printing position 40 to the slide inserting position 50 by the vertical moving piece 10b of the printing part 10. Therefore, the fan 17a mounting on the support part 17b can blow air to the slide glass 400 during the transportation from the printing position 40 to the slide inserting position 50.

As shown in FIGS. 4 and 5, the frosted area 400a of the slide glass 400 is disposed in the region at one end of the slide glass 400 so as to be adjacent to the smear region 400f in the length direction of the slide glass 400. A printable coating layer 400g formed of a coating agent such as resin or the like is formed on the frosted area 400a of the slide glass 400. The coating agent used to form the coating layer 400g has excellent durability against organic solvents such as alcohol, glycerin and the like which are used in the staining operation and microscopic examination. The previously mentioned two-dimensional barcode 400b and three line of text data (400c through 400e) are printed on the top surface of the coating layer 400g positioned in the frosted area 400a. The coating layer 400g also is formed to extend along the lengthwise direction of the slide glass 400 from the frosted area 400a so as to circumscribe the smear region 400f.

Figure 13:
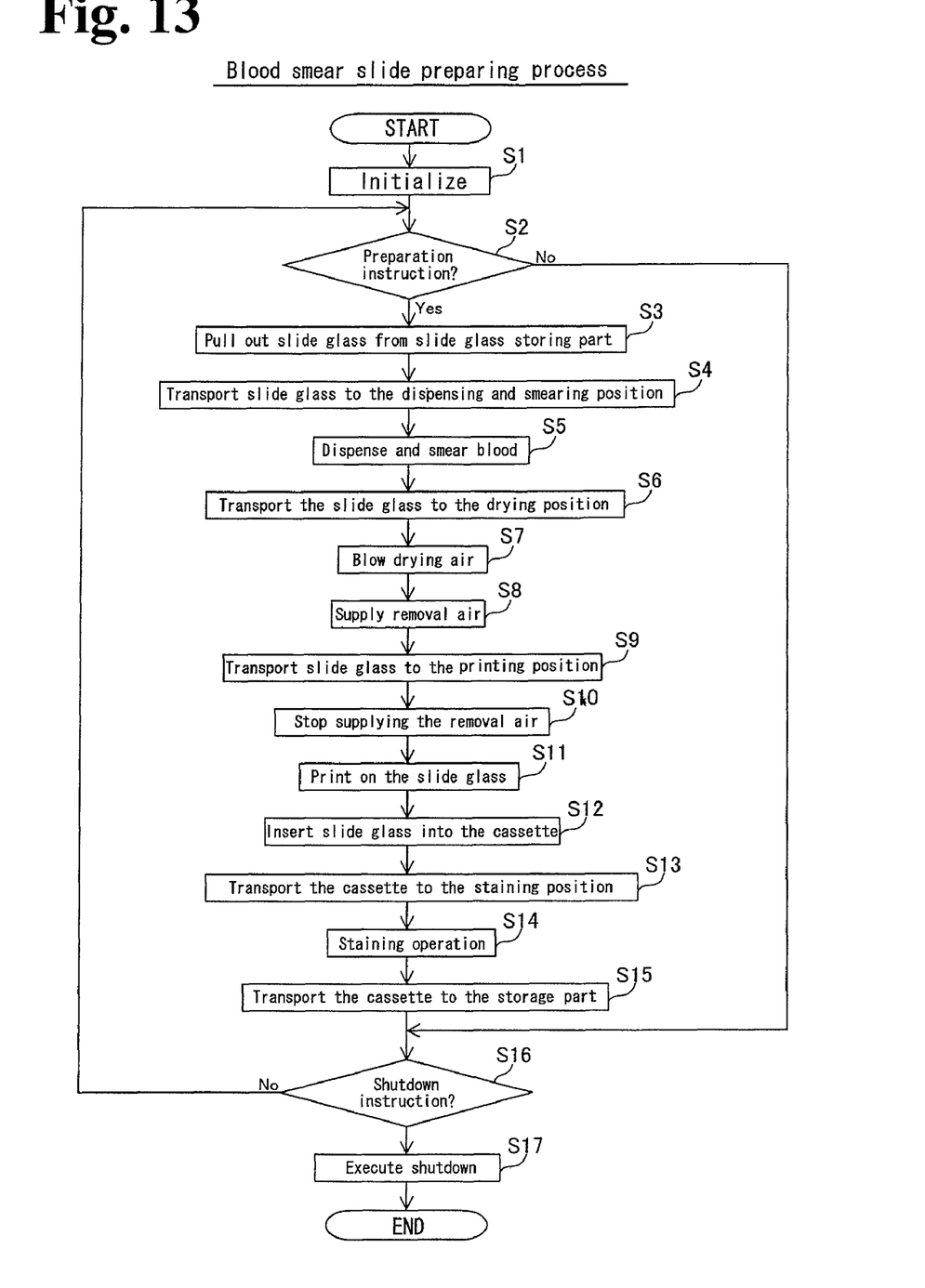
FIG. 13 is a flow chart showing the blood smear slide preparing process performed by the blood smear slide preparing apparatus of the embodiment shown in FIG. 1.

FIG. 13 is a flow chart showing the blood smear slide preparing process performed by the blood smear slide preparing apparatus of the embodiment shown in FIG. 1. The blood smear slide preparing process performed by the blood smear slide preparing apparatus 100 of the present embodiment is described below with reference to FIGS. 1, 3, 8, 11, and 13.

In the present embodiment, when a user presses the start switch 102 (refer to FIG. 1), the smear slide preparing program is initialized in the blood smear slide preparing apparatus 100 in step S1. In step S2, a determination is then made by the control unit 14 as to whether or not the user has issued a smear slide preparation instruction via the display and operation part 101. When there is no smear slide preparation instruction, the operation moves to step S16 and a determination is made by the control unit 14 as to whether or not the user has issued a shutdown instruction for the blood smear slide preparing apparatus 100. When there is a smear slide preparation instruction, however, a slide glass 400 within the slide storing part 11a is grabbed by the chuck of the first slide transporting part 12, and pulled out from the slide storing part 11a in step S3. In step S4, the slide glass 400 pulled from the slide storing part 11a is then moved onto the feed belt 13a of the second slide transporting part 13 by the first slide transporting part 12, and subsequently the slide glass 400 is transported to the dispensing and smearing position 20 by the feed belt 13a of the second slide transporting part 13.

In step S5, the blood is then dripped (dispensed) on the slide glass 400 using the pipette 1b (refer to FIG. 3). When preparing both a blood smear slide for automatic analysis and a blood smear slide for visual analysis, the same blood is dispensed to each of two slide glasses 400. An amount of blood corresponding to an automatic analysis blood smear slide is dispensed when preparing the blood smear slide for automatic analysis, and an amount of blood corresponding to a visual analysis blood smear slide is dispensed when preparing the blood smear slide for visual analysis. Thereafter, the blood dripped onto the slide glass 400 is smeared by the smear section 2. Specifically, the drawing glass 2a is moved so as to be in contact with the slide glass 400, and the blood dripped onto the slide glass 400 is smeared at the dispensing and smearing position 20 by reciprocatingly moving the drawing glass 2a in the length direction of the slide glass 400. In this case, the contact angle of the drawing glass 2a relative to the slide glass 400 and the speed of the reciprocating movement of the drawing glass 2a are regulated for the situation of preparing the blood smear slide for automatic analysis and the situation of preparing the blood smear slide for visual analysis.

In the subsequent step S6, the smeared slide glass 400 is transported to the drying position 30a (refer to FIG. 8) by the feed belt 13a. In step S7, the slide glass 400 which has been transported to the drying position 30a is then lifted upward a distance from the feed belt 13a by the lifting part 13b. Thus, the lifted slide glass 400 can be maintained at the drying position 30a without moving in the transport direction (arrow X direction) even when the feed belt 13a is driven to transport another slide glass 400. At the drying position 30a, the blood smeared on the slide glass 400 is air dried with cool air by the fan 15a. The cool air drying of the slide glass 400 is performed at the two adjacent drying positions 30a and 30b for approximately 30 seconds at each of the drying positions 30a and 30b.

The slide glass 400 which has been dried by cool air at the drying position 30b is then placed onto the feed belt 13a by the lifting part 13b. In the subsequent step S8, the control unit 14 opens the valve 16e (refer to FIG. 16), and removal air is supplied (discharged) from the nozzle 16a of the attached matter removing section 16 to the slide glass 400. In step S9, the slide glass 400 is then transported from the drying position 30b to the printing position 40 of the printing part 10 by the second slide transporting part 13. In the subsequent step S10, the control unit 14 closes the valve 16e to stop the supply of removal air from the valve 16a. With this arrangement the removal of the attached matter on the frosted area 400a is accomplished by the attached matter removing section 16 while the slide glass 400 is being transported from the drying position 30b to the printing position 40. As shown in FIG. 11, with this arrangement the removal air can contact across the entirety of the frosted area 400a by discharging the removal air to the frosted part 400a as the slide glass 400 is being transported regardless of whether the width W1 of the removal air discharged from the nozzle 16a of the attached matter removing section 16 at the frosted area 400a is smaller than the width W2 in the lateral direction of the slid glass 400. Furthermore, the discharge range (discharge angle) need not be greater than the predetermined angle γ (approximately 115 degrees) since the width W1 of the removal air at the frosted area 400a need not be greater than the width W2 of the slide glass 400. As a result, the removal air reaches the frosted area 400a without extreme reduction of the discharge force. Moreover, after the attached matter of the frosted area has been removed, the slide glass 400 continues being transported to the printing position 40.

In step S11, the two-dimensional barcode 400b which contains sample information such as the sample number, date, receiving date, name and the like, and three lines of text 400c which includes the date and patient name in Japanese characters are printing by the printing part 10 in the frosted area 400a from which the attached matter has been removed.

Thereafter, the printing ink is dried by the fan 17a while the slide glass 400 is moved to the slide inserting position 50 by the vertical moving piece 10b of the printing part 10. In step S12, the smeared slide glass 400 which has been moved to the slide inserting position 50 is then received in the cassette 3 of the slide glass inserting part 6.

In step S13, the cassette 3 which has received the slide glass 400 is transported to the staining part 7 by the cassette transporting member 5a, and the staining process is performed in step S14. In step S15, the cassette 3 is then transported to the storage part 9 or the blood sell automatic analyzer by the second cassette transporting part 8. In the subsequent step S16, a determination is made by the control unit 14 as to whether or not a user has issued a shutdown instruction; when a shutdown instruction has not been issued the operation moves to step S2. When a shutdown instruction has been issued, the shutdown is executed for the blood smear slide preparing apparatus 100 in step S17. The blood smear slide preparing process of the blood smear slide preparing apparatus 100 thus ends.

In the present embodiment described above, sample-related information is printed in the frosted area 400a of the slide glass 400 from which the attached matter has been removed after the matter attached to the frosted area 400a of the slide glass 400 has been removed by the attached matter removing section 16 even when matter such as glass shards and dust and the like are attached to the frosted area 400a of the slide glass 400 by removing the matter attached to the frosted area 400a of the slide glass 400 and thereafter printing the sample-related information on the frosted area 400a of the slide glass 400. As a result, sample-related information can be better printed in the frosted area 400a of the slide glass 400 by the printing part 10.

In the present embodiment, the attached matter removing section 16 does not touch the attached matter such as glass shards, dust and the like because the attached matter on the slide glass 400 is removed by discharging air from the attached matter removing section 16. There is therefore no need to clean the attached matter removing section 16, thus, maintenance of the device becomes simple.

In the present embodiment, attached matter on the frosted area 400a of the slide glass 400 can be removed without reducing the processing speed of the blood smear slide preparation because the matter attached to the frosted area 400a of the slide glass 400 is removed without stopping the transportation of the slide glass 400 by configuring the control unit 14 so as to control the operations of the attached matter removing section 16 and the second slide transporting part 13 so that the matter attached to the frosted area 400a of the slide glass 400 is removed as the second slide transporting part 13 is transporting the slide glass 400.

In the present embodiment, further attachment of matter to the frosted area 400a of the slide glass 400 can be prevented while the slide glass 400 is being transported to the printing position 40 after the attached matter has been removed because the transporting distance to the printing position 40 can be shortened after the attached matter has been removed by providing the attached matter removing section 16 near the printing position 40.

In the present embodiment, matter attached during the smearing of the blood can also be removed by the attached matter removing section 16 because the attached matter is removed after the sample has been smeared on the slide glass 400 by configuring the attached matter removing section 16 so as to remove the attached matter of the slide glass 400 while the slide glass 400 is being transported from the dispensing and smearing position 20 to the printing position 40.

In the present embodiment, the attached matter removing section 16 can remove attached matter which was attached when drying the smeared sample because the attached matter is removed after the smeared sample has dried on the slide glass 400 by providing the attached matter removing section 16 between the printing position 40 of the printing part 10 and the sample drying positions 30a and 30b of the fan 15a.

In the present embodiment, matter attached to the slide glass 400 when pulling the slide glass 400 from the slide glass storing part 11a can be removed by the attached matter removing section 16 by providing the attached matter removing section 16 between the slide storing part 11a of the slide supplying part 11 and the printing position 40 of the printing part 10.

Note that the embodiment of the present disclosure is in all aspect an example and should not be considered to be limiting. The scope of the present invention is defined by the scope of the claims and not be the description of the embodiment, and includes all modifications within the scope of the claims and the meanings and equivalences therein.

For example, although the present embodiment describes a blood smear slide preparing apparatus as an example of a smear slide preparing apparatus, the present invention is not limited to this example inasmuch as the smear slide preparing apparatus may be an apparatus other than a blood smear slide preparing apparatus.

Although the above embodiment describes and example in which the attached matter such as glass shards, dust and the like on the slide glass is removed by discharging air on the slide glass, the present invention is not limited do this example inasmuch as attached matter on the slide glass may also be removed by a brush. When a brush is used, the attached matter removed from the slide glass can be collected at a predetermined location to prevent the dispersion of the attached matter within the apparatus. Furthermore, the attached matter on the slide glass may also be removed by adhering the attached matter to an adhesive tape, or removing and collecting the attached matter on the slide glass air suction using a negative pressure. When removing attached matter using an adhesive tape or air suction, it is possible to prevent dispersion of the attached matter on the slide glass within the apparatus and prevent airborne dispersion of the dust.

Although the above embodiment has been described in terms of providing a printing part for printing a barcode and text data containing information such as sample number and date and the like on the slide glass as an example of a sample-related information providing part, the present invention is not limited to this example inasmuch as a affixing part may also be provided for affixing a label containing a printed barcode and text data to the slide glass.

Although the above embodiment is described by way of example in which attached matter on a slide glass is removed after a sample is smeared on the slide glass, the present invention is not limited to this example inasmuch as attached matter on the slide glass may also be removed before a sample is smeared on the slide glass insofar as the attached matter is removed before the sample-related information is provided on the slide glass. For example, the sample may be smeared after the attached matter on the slide glass has been removed, and the sample-related information may be thereafter provided on the slide glass; and the sample-related information may be provided on the slide glass after the attached matter has been removed, and the sample may thereafter be smeared.

Although the above embodiment has been described by way of example in which the attached matter removing section is disposed adjacent to the printing part, the present invention is not limited to this example inasmuch as the attached matter removing section in the slide glass transporting paths of the first slide transporting part and the second slide transporting part.

Although the above embodiment has been described by way of example of preparing a blood smear slide in which blood is smeared on a slide glass, the present invention is not limited to this example inasmuch as a smear slide may also be prepared using biological tissue such as urine or cells collected from the uterine cervix.

Although the above embodiment has been described by way of example using a pressure supplied from a single air pressure source in predetermined parts other than the attached-matter removing section and the nozzle of the attached matter removing section, the present invention is not limited to this example inasmuch as a separate air pressure source may also be provided for the attached matter removing section.

Although the above embodiment is described by way of example in which removal air is discharged on the slide glass from an angle of approximately 45 degrees, the present invention is not limited to this example inasmuch as the removal air may also be discharged on the slide glass at another angle.

Although the above embodiment describes the printing part being configured by a thermal transfer printer, the present invention is not limited to this example inasmuch as the printing part 10 may also be configured by, for example, a dot matrix printer or laser printer.

What is claimed is:

1. A smear slide preparing apparatus comprising:
    a smear section configured to smear a sample on a first area on a slide glass;
    a sample-related information providing section configured to provide sample-related information which is related to the sample on a second area on the slide glass, wherein the second area is different from the first area;
    an attached matter removing section which comprises a nozzle and an air pressure source connected to the nozzle, and jets a removal air to the second area on the slide glass by supplying an air pressure to the nozzle with the air pressure source to remove attached matter which is attached to the second area on the slide glass; and
    a controller configured to control the smear section, the attached matter removing section and the sample-related information providing section so as to jet the removal air to the second area on the slide glass after smearing the sample on the first area on the slide glass, and subsequently provide the sample-related information on the second area on the slide glass.

2. The smear slide preparing apparatus of claim 1, further comprising
    a drying section which comprises a fan which blows an air to the sample smeared on the slide glass to dry the sample, wherein
    the controller controls the drying section and the attached matter removing section so as to blow the air to the smeared sample with the fan and subsequently jet the removal air to the second area on the slide glass.

3. The smear slide preparing apparatus of claim 2, wherein the attached matter removing section is arranged between a sample drying position of the drying section and a sample-related information providing position of the sample-related information providing section.

4. The smear slide preparing apparatus of claim 1, wherein the sample-related information providing section comprises a printing part configured to print the sample-related information on the second area on the slide glass.

5. The smear slide preparing apparatus of claim 4, wherein the printing part is a thermal transfer printer configured to print the sample-related information on a printable coating layer formed on the second area on the slide glass.

6. The smear slide preparing apparatus of claim 1, further comprising:
    a slide storing section for storing a plurality of slide glasses on each of which a sample is to be smeared by the smear section;
    a first slide transporting part for transporting a slide glass from the slide storing section to a sample smearing position of the smear section; and
    a second slide transporting part for transporting the slide glass on which a sample is smeared by the smear section from the sample smearing position to a sample-related information providing position of the sample-related information providing section, wherein
    the attached matter removing section is arranged in a slide glass transport path of the second slide glass transporting part.

7. The smear slide preparing apparatus of claim 1, further comprising:
    a slide storing section configured to store a plurality of slide glasses on each of which a sample is to be smeared by the smear section; and
    a slide transporting part configured to transport a slide glass stored in the slide storing section to a sample-related information providing position of the sample-related information providing section wherein
    the controller is configured so as to control the slide transporting part and the attached matter removing section so as to jet the removal air to the second area on the slide glass while transporting the slide glass.

8. The smear slide preparing apparatus of claim 7, wherein the controller is configured so as to control the slide transporting part and the attached matter removing section so as to transport the slide glass to the sample-related information providing position by continuing a transportation of the slide glass after jetting the removal air while transporting the slide glass.

9. The smear slide preparing apparatus of claim 1, wherein the nozzle is arranged so as to jet the removal air to the second area from a direction which is inclined at a predetermined angle relative to a surface of the slide glass.

10. The smear slide preparing apparatus of claim 9, wherein the nozzle is arranged so as to jet the removal air to the second area from the first area side.

11. The smear slide preparing apparatus of claim 1, wherein
    the air pressure source is used by a drive part other than the attached matter removing section.

12. The smear slide preparing apparatus of claim 1, wherein
    the attached matter removing section is provided near a sample-related information providing position of the sample-related information providing section.

* * * * *